United States Patent [19]

Quick

[11] 4,390,442
[45] Jun. 28, 1983

[54] NON-STINGING EYE MAKE-UP REMOVER COMPOSITION

[75] Inventor: Timothy W. Quick, Memphis, Tenn.

[73] Assignee: Plough, Inc., Memphis, Tenn.

[21] Appl. No.: 258,184

[22] Filed: Apr. 27, 1981

[51] Int. Cl.³ .......................... C11D 3/48; C11D 1/18
[52] U.S. Cl. ................................... 252/106; 252/153; 252/547; 424/326
[58] Field of Search ....................... 252/106, 153, 547; 424/326

[56] References Cited

U.S. PATENT DOCUMENTS

| | | | |
|---|---|---|---|
| Re. 29,693 | 7/1978 | Phares | 424/326 |
| 3,855,140 | 12/1974 | Billany et al. | 252/547 |
| 3,960,745 | 6/1976 | Billany et al. | 252/547 |
| 4,013,576 | 3/1977 | Loshaek | 252/547 |
| 4,196,201 | 4/1980 | Boelle et al. | 424/180 |

OTHER PUBLICATIONS

Maybelline Co. "Maybelline 100% Oil Free Eye Make-Up Remover", 1979.
N. Senior, Some Observations on the Formulation and Properties of Chlorhexidine, U. Soc., Cosmet. Chem. 24 259-278 (1973).
Remington's Pharmaceutical Sciences, Mack Publishing Co., 1970, pp. 1331, 1332, 1572, 1573.
Plough, Inc. Approved Formula, Eye Make-Up Remover, Non Oily.
The Condensed Chemical Dictionary, 7th Ed. Reinhold Publishing Corp., New York, p. 765.
Mullins, "Eye Lotions", Cosmetics: Science and Technology, vol. 2, 1972, p. 590.
Schimmel et al., "Preservation of Cosmetics", Cosmetics: Science and Technology, vol. 3, 1974, pp. 424-425.

Primary Examiner—S. L. Childs
Attorney, Agent, or Firm—Warrick E. Lee, Jr.; Vincent H. Gifford; Bruce M. Eisen

[57] ABSTRACT

A non-stinging composition for removing make-up from the area near the eye comprising cleanser, buffering agent, water, chlorhexidine digluconate, and phenethyl alcohol.

13 Claims, No Drawings

NON-STINGING EYE MAKE-UP REMOVER COMPOSITION

This invention relates to aqueous compositions for removing make-up, such as eye shadow, foundation, cold cream, mascara, eye liner and the like, from the area near the eye.

Prior-art compositions, particularly those containing sufficient amounts of parabens for preservation, sting the eyes upon accidental contact. Removal of make-up from the area near the eye almost always causes some of the make-up remover to accidently contact the eye. The present invention comprises an aqueous composition with a preservative system that is far less stinging. The present invention also has the desirable property of being non-oily.

In its broadest aspect, the present invention comprises a non-stinging composition for removing make-up from the area near the eye comprising:
a. cleanser for removing make-up,
b. buffering agent sufficient to control the pH of the composition to between about 6 and 8 after compounding,
c. water,
d. from about 0.005 to 0.1 percent chlorhexidine digluconate, and
e. from about 0.01 to 0.5 percent phenethyl alcohol.

As used throughout the present specification and claims, the term "non-stinging" is intended to describe a composition capable of removing make-up which, upon accidental contact with the eye, is found by a majority of users, to be either non-stinging or considerably less stinging than prior-art compositions preserved with effective amounts of parabens.

Terms used to describe ingredients in the compositions conform to those of the CTFA Cosmetic Ingredient Dictionary, Second Edition, published by the Cosmetic, Toiletry and Fragrance Association, Inc., 1133 Fifteenth Street, N.W., Washington, D.C. 20005. The relevant contents of this dictionary are incorporated herein by reference.

For convenience, the definitions of specific ingredients are reproduced here:

Amphoteric-5 and Amphoteric 6 are two grades of a long chain imidazoline type of zwitterion conforming generally to the formula:

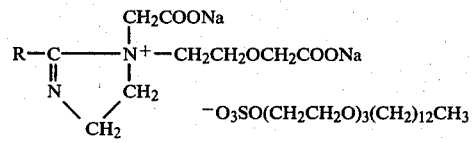

where R is derived from the coconut fatty radical.

Amphoteric-9 is a long chain imidazoline type of zwitterion conforming generally to the formula:

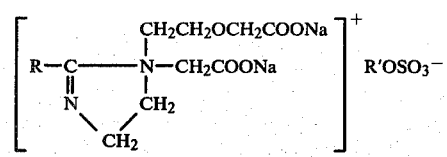

where R is derived from the coconut fatty radical and R' is derived from a mixture of lauryl and laureth-3 radicals.

Amphoteric-14 is a long chain imidazoline type of zwitterion conforming generally to the formula:

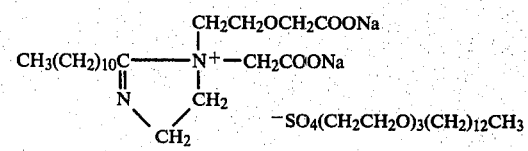

Polysorbate 20 is a mixture of laurate esters of sorbitol and sorbitol anhydrides, consisting predominantly of the monoester, condensed with approximately 20 moles of ethylene oxide. It conforms generally to the formula:

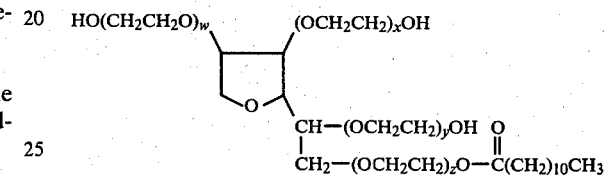

where $w+x+y+z$ has an average value of 20.

Unless stated otherwise, all percents are weight percents based on the total weight of the composition.

DETAILED DESCRIPTION OF THE INVENTION

This invention is predicated on the discovery that a very selective combination of two known preservatives in low concentrations is capable of preserving the composition from degradation by microorganisms. The novel preservative system does not render the compositions stinging to the eyes, as do conventional preservative systems based on parabens present in amounts sufficient for preservation.

The first preservative is chlorhexidine digluconate, available in an aqueous solution of 20 grams chlorhexidine digluconate per 100 ml of solution, sold as "chlorhexidine gluconate" by Lonza, Inc. Chlorhexidine digluconate is particularly effective against bacteria.

The chlorhexidine digluconate is preferably present in the composition in the amount of about 0.005 to 0.1 percent, more preferably about 0.005 to 0.05 percent. These amounts are based on water-free chlorhexidine digluconate.

By itself, the chlorhexidine digluconate is incapable of preserving the composition in amounts that do not cause stinging. However, when combined with a selected second preservative, the surprising result of preservation with amounts low enough to prevent stinging is achieved. The second preservative is phenethyl alcohol (2-phenylethanol). The preferred amount of the phenethyl alcohol is from about 0.01 to 0.5 percent, more preferably about 0.02 to 0.2 percent. Phenethyl alcohol is particularly effective against molds and yeasts.

Any cleanser compatable with the other ingredients and capable of removing make-up without rendering the composition stinging is acceptable. Nonionic or quaternary cleansers are preferred. Of the quaternary type cyclic compounds, such as amphoteric-5, amphoteric-6, and amphoteric-9, are believed acceptable. The most preferred cleanser is amphoteric-14, sold under the trade name MIRANOL 2MHT Mod. by the Miranol Chemical Co. The concentrations of the cleanser are preferably from about 5 to 15 percent, more preferably about 5 to 10 percent.

The cleansing action of amphoteric-14 can be considerably enhanced by including polysorbate 20 in the composition. The polysorbate 20, sold under the trade name TWEEN 20 by ICI United States Inc., is preferably present in the amount of from about 0.5 to 3 percent.

At least some emollient is preferably present in the composition to avoid discomfort to the eyelids. The preferred emollient is propylene glycol. Other emollients such as butylene glycol, glycerine, sorbitol and mixtures thereof are acceptable. The preferred concentration of emollient is about 1 to 3 percent.

Buffering agent to control the pH of the composition to between 6 and 8 after compounding (more preferably about 6.5. to 7.5, and most preferably about 7) is required. From about 0.5 to 2 percent boric acid is preferred.

Although ordinary tap water may be acceptable in some localities, it is preferable to use water purified by deionization, etc. The preferable water content is from about 80 to 95 percent, with about 85 to 90 percent being more preferred.

EXAMPLE

A make-up remover in accordance with the invention having the following composition is prepared:

| Ingredients | Amount (%) |
| --- | --- |
| amphoteric-14 | 7.5 |
| polysorbate 20 | 1.5 |
| propylene glycol | 1.5 |
| boric acid | 1.3 |
| water | 88.1 |
| chlorhexidine digluconate (20% w/v aqueous solution)* | 0.05 |
| phenethyl alcohol | 0.05 |

*A solution containing 20 grams of chlorhexidine digluconate per 100 ml of solution. Hence the amount of water-free chlorhexidine digluconate in the composition is about 0.01 percent, and the solution's total water content is about 88.14 percent.

All of the ingredients except the two preservatives are blended at temperature of about 45° C. Next, the chlorhexidine digluconate solution and phenethyl alcohol are mixed in. The composition is cooled to room temperature and the pH is 7.

When used to remove make-up from the area near the eye, a majority of users find the composition of the example to be either non-stinging or substantially less stinging upon accidental contact with the eyes than a prior-art composition preserved with an effective amount of parabens.

What is claimed is:

1. A non-stinging composition for removing make-up from the area near the eye comprising:
   a. cleanser for removing make-up,
   b. buffering agent sufficient to control the pH of the composition to between 6 and 8 after compounding,
   c. water,
   d. from 0.005 to 0.1 percent chlorhexidine digluconate, and
   e. from 0.01 to 0.5 percent phenethyl alcohol.

2. The composition of claim 1 comprising
   a. from 5 to 15 percent cleanser,
   b. buffering agent sufficient to control the pH of the composition to between 6.5 and 7.5,
   c. 80 to 95 percent water
   d. from 0.005 to 0.05 percent chlorhexidine digluconate, and
   e. about 0.02 to 0.2 percent phenethyl alcohol.

3. The composition of claim 2 comprising
   a. from 5 to 10 percent cleanser
   b. buffering agent sufficient to control the pH of the composition to 7,
   c. from 85 to 90 percent water,
   d. 0.01 percent chlorohexidine digluconate, and
   e. 0.05 percent phenethyl alcohol.

4. The composition of claim 3 wherein the amount of cleanser is 7.5 percent and the amount of water is 88.1 percent.

5. The composition of claim 1 wherein said cleanser is selected from the group consisting of nonionic cleansers and quaternary cleansers.

6. The composition of claim 5 wherein said cleanser is a cyclic quaternary compound.

7. The composition of claim 6 wherein said cleanser is

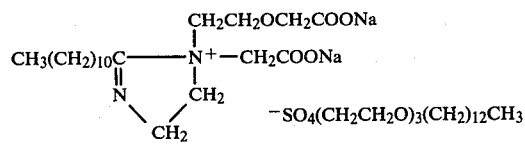

8. The composition of claim 7 further comprising polysorbate 20.

9. The composition of claim 8 further comprising emollient selected from the group consisting of propylene glycol, butylene glycol, glycerine, sorbitol and mixtures thereof.

10. The composition of claim 9 wherein said emollient is propylene glycol.

11. A non-stinging composition for removing make-up from the area near the eye comprising by weight, based on the total weight of the composition:
(1) from 5 to 15 percent

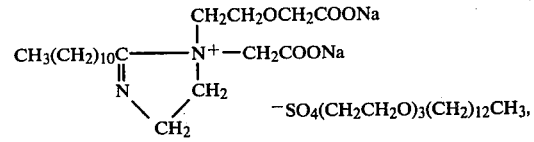

(2) from 0.5 to 3.0 percent polysorbate 20,
(3) from 1 to 3 percent propylene glycol,
(4) from 0.5 to 2 percent boric acid,
(5) from 85 to 90 percent water,
(6) from 0.005 to 0.05 percent chlorhexidine digluconate, and
(7) from 0.02 to 0.2 percent phenethyl alcohol.

12. A non-stinging composition for removing make-up from the area near the eye comprising by weight, based on the total weight of the composition:
(1) 7.5 percent

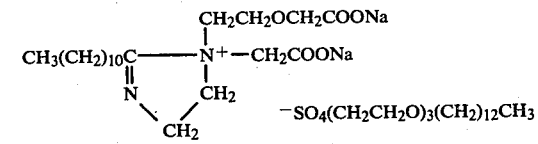

(2) 1.5 percent polysorbate 20, (3) 1.5 percent propylene glycol, (4) 1.3 percent boric acid, (5) 88.1 percent water, (6) 0.01 percent chlorhexidine digluconate, and (7) 0.05 percent phenethyl alcohol.

13. A non-stinging composition for removing make-up from the area near the eye comprising by weight, based on the total weight of the composition:

(1) 7.5 percent

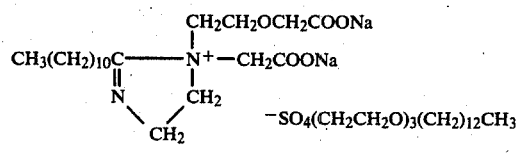

(2) buffering agent sufficient to control the pH of the composition to between 6.5 and 7.5 after compounding, (3) 1.5 percent propylene glycol, (4) 85 to 90 percent water (5) 1.5 percent polysorbate 20

(6) 0.01 percent chlorhexidine digluconate, and (7) 0.05 percent phenethyl alcohol.

* * * * *